United States Patent
Wikeley et al.

(10) Patent No.: US 10,485,237 B2
(45) Date of Patent: Nov. 26, 2019

(54) USE OF A CHEMICAL AGENT FOR THINNING OF STONE FRUIT

(71) Applicant: FINE AGROCHEMICALS LIMITED, Whittington (GB)

(72) Inventors: Philip Simon Wikeley, Malvern (GB); Joëlle Reignard, Meyzieu (FR); Kevin Forney, Bakersfield, CA (US)

(73) Assignee: FINE AGROCHEMICALS LIMITED, Whittington (GB)

( * ) Notice: Subject to any disclaimer, the term of this patent is extended or adjusted under 35 U.S.C. 154(b) by 51 days.

(21) Appl. No.: 15/110,750

(22) PCT Filed: Jan. 8, 2015

(86) PCT No.: PCT/EP2015/050272
§ 371 (c)(1),
(2) Date: Jul. 11, 2016

(87) PCT Pub. No.: WO2015/104344
PCT Pub. Date: Jul. 16, 2015

(65) Prior Publication Data
US 2016/0330961 A1    Nov. 17, 2016

(30) Foreign Application Priority Data
Jan. 9, 2014  (EP) ..................................... 14150671

(51) Int. Cl.
*A01N 45/00* (2006.01)
*A01N 43/12* (2006.01)

(52) U.S. Cl.
CPC .............. *A01N 45/00* (2013.01); *A01N 43/12* (2013.01)

(58) Field of Classification Search
CPC ................................ A01N 45/00; A01N 43/12
See application file for complete search history.

(56) References Cited

U.S. PATENT DOCUMENTS

| | | |
|---|---|---|
| 2,957,760 A | 10/1960 | Tafuro et al. |
| 4,936,901 A | 6/1990 | Surgant, Sr. et al. |
| 5,125,959 A | 6/1992 | Suyama et al. |
| 5,163,993 A | 11/1992 | Shafer et al. |
| 5,622,658 A | 4/1997 | Lloyd et al. |
| 5,622,915 A | 4/1997 | Buendia et al. |
| 6,387,388 B1 | 5/2002 | Misselbrook et al. |
| 2002/0114821 A1 | 8/2002 | Lescota et al. |
| 2010/0016165 A1 | 1/2010 | Wang et al. |
| 2012/0088668 A1 | 4/2012 | Williams et al. |

FOREIGN PATENT DOCUMENTS

| | | |
|---|---|---|
| EP | 089205 A2 | 9/1983 |
| EP | 0252897 A2 | 1/1988 |
| EP | 463241 A1 | 1/1992 |
| GB | 1509195 A | 5/1978 |
| WO | 01/62080 A1 | 8/2001 |

OTHER PUBLICATIONS

Ostreiko et al., Cherry tree prepn. before mechanical trimming of crown reduces the number of dried off brances after cutting, by applying solution of gibberellic acid in concentrations of 0.01-0.03 percent; SU 704526A, Derwent Abstract, 1979, 2 pages.*
European Search Report for priority application EP14150671.7 dated Mar. 18, 2014.
International Search Report for PCT/EP2015/050272 dated Mar. 13, 2015.
International Preliminary Report on Patentability for PCT/EP2015/050272 dated Jul. 12, 2016.
Soutwick et al, "Controlling Cropping in 'Loadel' Cling Peach Using Gibberellin: Effects on Flower Density, Fruit Distribution, Fruit Firmness, Fruit Thinning, and Yield", J. Amer. Soc. Hort. Sci. 120(6): 1087-1095 (1995).
Southwick et al, "Reducing Flowering with Gibberellins to Increase Fruit Size in Stone Fruit Trees: Applications and Implications in Fruit Production", HortTechnology, Oct.-Dec. 2000, 10(4), p. 744-751.
González-Rossia et al, "Horticultural factors regulating effectiveness of GA3 inhibiting flowering in peaches and nectarines (*Prunus persica* L. Batsch)", Scientia Horticulturae 111 (2007) 352-357.
Southwick, "Use of gibberellins to reduce flowering in stone fruit: toward reducing the need for hand thinning", Proceedings—Plant Growth Regulation Society of America, 26th, 1999, p. 50-55.

(Continued)

*Primary Examiner* — John Pak
*Assistant Examiner* — Andriae M Holt
(74) *Attorney, Agent, or Firm* — Ramin Amirsehhi; David P. Owen

(57) ABSTRACT

The invention relates to the use of gibberellin 7 (GA7) for thinning of stone fruit, wherein the use comprises applying the GA7 to stone fruit in a first year by foliar spray within 12 weeks after full bloom, to achieve thinning in the following year. The stone fruit can be peach, nectarine, apricot, cherry, mirabelle or plum, preferably peach or nectarine. GA7 is used or applied in the period of 4 to 12 weeks after full bloom in the first year. The GA7, if used in admixture with GA4, has relative amounts of GA7 to GA4 of 70% GA7 or more and 30% GA4 or less.

13 Claims, No Drawings

(56) References Cited

OTHER PUBLICATIONS

Oliveira et al, "Gibberellin structure-activity effects on flower initiation in mature tr TI—Gibberellin structure-activity effects on flower initiation in mature trees and on shoot growth in mature and juvenile *Prunus avium*", Plant Growth Regulation 13: 55-63, 1993.

Singh et al, "Gibberellin A4/A7 improved fruit set, retention, yield and quality of subtropical peach (*Prunus persica* Batsch)", Proc. of the Int. Conf. on Integrated Food Prod., Acta Hort. 525, ISHS 2000, p. 467-469.

Singh et al, "Effects of gibberellin A4/A7 and blossom thinning on fruit set, retention, quality, shoot growth and return bloom of phalsa (*Grewia asiatica* L.)", Proc. of the Int. Conf. on Integrated Food Prod., Acta Hort. 525, ISHS 2000, p. 463-466.

Wilkie et al, "Regulation of floral initiation in horticultural trees", Journal of Experimental Botany, vol. 59, No. 12, pp. 3215-3228, 2008.

Mutasa-Göttgens et al, "Gibberellin as a factor in floral regulatory networks", Journal of Experimental Botany, vol. 60, No. 7, pp. 1979-1989, 2009.

\* cited by examiner

USE OF A CHEMICAL AGENT FOR THINNING OF STONE FRUIT

CROSS REFERENCE TO RELATED APPLICATIONS

This application is a U.S. National Stage under 35 USC 371 of PCT application number PCT/EP2015/050272 filed on 8 Jan. 2015, which claims priority from EP application number 14150671.7 filed on 9 Jan. 2014. Both applications are hereby incorporated by reference in their entireties.

FIELD OF THE INVENTION

The invention relates to the use of a chemical agent for thinning of stone fruit. Further, the invention relates to a method of thinning stone-fruits in trees.

BACKGROUND OF THE INVENTION

Stone fruit, like apricot, nectarine, plum, cherry and peach are grown in orchards. Under average growing conditions, pollination (self or cross) is very efficient and many fruits are obtained. However, the fruit carrying capacity of trees is limited and, hence, the increase of number of fruit is accompanied by reduction in fruit size. Since small fruit is qualified in the fresh fruit market as low quality fruit and are directed to industry at very low prices, it is common practice among fruit growers to reduce the number of fruits per tree by chemical, mechanical and/or hand thinning in order to prevent branch breakage, and to obtain large, high quality fruits. Also, abundant bearing may cause bi-annual bearing, which is disadvantageous by itself.

The need for fruit load control is widely recognised in stone fruit. Research on chemical fruit thinning has had limited success so far. Therefore growers are left with very few options: (i) flower hand thinning which requires a lot of man power and is very expensive, (ii) fruit hand thinning which is typically done 4-6 weeks after full bloom and requires a lot of man power and this is therefore very expensive, (iii) mechanical flower thinning which is done during flowering; but this has some downsides: difficulty to evaluate the thinning intensity, risk of tree damages, not good repartition of removed flowers, which results in difficult fruit coloration, or additional manually removing of leaves to let the light inside the canopy. Therefore, grower practice for the moment can be summarised as follows: (i) On some varieties, mechanical flower thinning is done in order to remove part of the flowers and to limit hand thinning later on. Depending on the crop/variety, this can be 50-150 h/ha (h/ha=hours of hand-thinning per ha). This is mainly done on very fertile peach/nectarin varieties like Carène, Gardeta, Garcica, Ivory Star, Lorinda, Early Top, and Valley Sweet. It is used also on young trees ($3^{rd}$ leaf). (ii) On all varieties, fruit thinning is done by hand in the early stages of fruit development. This is estimated to represent 50-250 h/ha depending on the varieties. Thus, together, the work load for flower+fruit thinning is commonly estimated between 200 and 250 h/ha in average but can reach up to 400 h/ha. Because of the high labour cost, chemical thinning operations is sought for, provided it gives stable results.

A number of chemical compounds have been suggested to be suitable for thinning stone fruit. Examples of suggested chemical thinning agents are e.g. described in:

- U.S. Pat. No. 2,957,760, alpha-(3-chlorophenoxy)-propionic acid and its salts;
- GB1509195, combinations of auxin, gibberellin 3 and a urea-derivative;
- EP089205, 2-pyrrolidone-5-carboxilic acid, N-mixed fatty acylated L-glutamic acid sodium salt or fatty acylated sugar molecules;
- EP463241, certain alkoxylated amines;
- U.S. Pat. No. 5,622,915, 3,5,6-trichloro-2-pyridyloxy-acetic acid or salts thereof
- US2012/088668, anthranilic acid and/or acetophenon, optionally in combination with auxins In practise, only very few products are available for stone fruit. These products include (i) GA3 based products. In Spain, a 3.6% GA3 formulation is used: Ralex from Kenogard and Laikuaj from Cequisa on an authorised rate of 0.18-0.25%. The authorised use is to improve fruit size and reduce flowering in peach. The timing of treatment indicated in the registration notice is 4 and 2 weeks before harvest. Ralex is also authorized in Australia for use in stone fruit (apricots, nectarin and peach, at 70-400 ml/100 for a 40 g/L GA3 formulation applied from early December to late January); (ii) GA3 based products (Berelex and Gibb 3) are authorised in France to modify fruit set level in peach. Dose is 4-6 tablets/100 (4-6 g/L) for Berelex applied during floral induction. (iii) NAA (naphthalene acetic acid, a synthetic auxin) is used in Italy (Fixormon: 85 g/L NAA) and is authorised for peach thinning at 12-20 mL/100 with an application timing when fruitlet are 10-15 mm in diameter.

Of all the suggested chemical treatments, only the treatment with GA3 (gibberellic acid) is relatively common. GA3 is also available as tablets (Falgro). Literature references are for example: Southwick et al. J. Amer. Soc. Hort. Sci. 120(6) (1995) 1087-1095; Southwick & Glozer, Hortechnology, 10(4) (2000); and González-Rossia et al. Scientia Horticulture 111 (2007) 352-357.

Southwick in the $26^{th}$ Proceedings PGR society of America, (1999), pp 50-55 also reports on the use of Ralex (GA3) on several stone fruit cultivars. Accidentally, the paper comprises one table wherein effect of GA3 is compared with GA4 and with GA7 when applied on an apricot variety in May or June. The source and purity of GA4 or GA7 are unclear. Further, the paper explains that GA4 is more effective than either GA3 or GA7. GA7 shows only in 1 out of 6 experiments a non significant reducing effect on flowering and in 4 experiments out of 6 shows the opposite effect of increased flowering (significant vs. untreated).

Oliveira and Browning in Plant Growth Regulation (1993) 13:53-63 report on effects on flower initiation of a number of gibberellins. These GAs are applied as 10 µl of a 60% aqueous ethanol solution between the points of bud insertion in the 6-8 consecutive distal areas of individual fruiting spurs, i.e. on the shoots between the buds.

Acta Horticulturea (2000) comprises the Proc. Of the Int Conf on integrated fruit Production (1998), 525:467-469, XP-002720822, and 525:463-466, XP-002720823, wherein Singh et al. describe experiments on GA4-GA7 mixtures, which mixtures are generally about 50/50. The treated crop Phalsa was sprayed at fully swollen flower bud stage and none of the treatments inhibited the return bloom in this crop.

Despite these and other experiments, no suitable alternatives are known to date.

Hence, there is a clear need for a further improved stone fruit thinning agent.

SUMMARY OF THE INVENTION

It is an object of the invention to provide a chemical thinning treatment of stone fruits which allows for at least comparable but preferably better thinning results in stone fruit species.

This invention provides for the use of gibberellin 7 (GA7) for thinning of stone fruit by applying the GA7 as foliar spray within 12 weeks after full bloom, the GA7 if used in admixture with GA4, has relative amounts of GA7 to GA4 of 70% GA7 or more and 30% GA4 or less.

The invention furthermore provides for a method for thinning stone fruit, by applying a suitable amount of GA7 as foliar spray within 12 weeks after full bloom to a tree in a first year, preferably in the period of 4 to 12 weeks after full bloom, to achieve reduced flowering the second year, the GA7 if used in admixture with GA4, has relative amounts of GA7 to GA4 of 70% GA7 or more and 30% GA4 or less.

Preferably, GA7 is used as a formulation with 0.5-4 wt % of GA7. The formulation preferably is a liquid. Such liquid formulation may be applied in an amount of 0.1 L-3 per 100 spraying fluid, more preferably 0.3-1.5 L/100.

Preferably, the amount per hectare of GA7 is between 0.5-10 Liter of the liquid formulation.

Preferably, the amount of GA7 applied per hectare is between 0.2-100 g/ha.

Suitable stone fruit include peach, apricot, nectarine, plum, cherry and mirabelle, and the preferred species are peach and nectarine.

The tests show that with suitable application of GA7 (which may include single or multiple treatments), an about 30% reduction (between 10-40%) is achievable, and a reduction in manual thinning of about 30% as well. Further tests showed even higher thinning efficiency. The resultant fruit was of the same quality as fully hand-thinned fruit.

Hence, the present invention also provides for a method of growing stone fruit wherein the method for thinning according to the invention is used, and the fruit is harvested in the second year

DETAILED DESCRIPTION OF THE INVENTION

This invention provides for the use of gibberellin 7 (GA7) for thinning of stone fruit by applying the GA7 as foliar spray within 12 weeks after full bloom, the GA7 if used in admixture with GA4, has relative amounts of GA7 to GA4 of 70% GA7 or more and 30% GA4 or less.

Suitable stone fruit include peach, apricot, nectarine, plum, cherry or mirabelle, and the preferred species are peach and nectarine as peach and nectarine exhibit the largest thinning problem.

Gibberellins are one class of plant growth regulators which are diterpenoid acids. Gibberellins are commercially produced by fermentation of a natural fungus, *Gibberella fugikuroi*. Gibberellins are marketed under various trade names and are commercially used on a variety of fruit orchards, vegetable crops, row crops, and ornamental crops. The predominantly used gibberellic acid is GA3. Nowadays, over 120 gibberellins are known. One other used gibberellin is a combination of two, (GA4+7). Due to diterpenoid structure of gibberellins containing double bonds and cyclic lactone, they are less stable in water.

For a long time people have realized that the flowering of plants is a complicated developmental process that involves a series of morphological and physiological stages under the control of a number of external signals and internal factors. Among all factors that control plant flowering, photoperiod and plant hormones have been studied in great detail. Genes have been identified that genetically control floral organ identity and development. The expression of these genes was found to be regulated by photoperiod and hormones. Thus, flowering is a highly complex biological mechanism, involving many regulators. This is probably the reason why only very few chemical thinning agents are suitable in practice.

Unexpectedly, GA7 gives reliable thinning results in stone fruit when applied by spraying on fruit trees, within 12 weeks after full bloom.

GA7 may be used in admixture with GA4, but the relative amounts of GA7 to GA4 are 70% GA7 or more and 30 GA4 or less. Preferably, the GA7 contains less than 10 wt % of GA4 relative to the GA7, more preferably less than 5 wt %. Unless otherwise specified, GA7 includes all grades from GA7/GA4 100/0 to 70/30, however, amounts given below for GA7 relate to GA7 only, and do not include the amount of GA4 that may be present. It appeared that GA7/GA4 mixtures with equal amounts of GA7 and GA4 as for example described in the Sing references mentioned before, do not give reliable fruit thinning results. In some years, some thinning is observed, but this effect is not consistently achieved. Hence, GA7 can only reliably be used for thinning as relatively pure compound (i.e. low amount of GA4 present).

The invention furthermore provides for a method for thinning stone fruit, by applying a suitable amount of GA7 as foliar spray within 12 weeks after full bloom to a tree in a first year, to achieve reduced flowering the second year.

The GA7 is applied by spraying on the fruit-trees, and the spray will mainly be on the leaves. Spraying on trees is generally known as "foliar spray".

The GA7 can be applied once, or multiple times per year. In case GA7 is applied more than once, the period between the application can be between for example 1-8 weeks, preferably between 1-4 weeks apart, such as for example 2 weeks apart, 3 weeks apart or the like.

The GA7 preferably is applied in the period of 4 to 12 weeks, preferably 6-12, most preferably 8-12 weeks, after full bloom. Full bloom is a common term in the art, and is defined as the day on which at least 50% flowers are open, and the first petals are falling. In case GA7 is applied more than once, at least the first application is done within 12 weeks after full bloom. Preferably all sprays are done before the 12 week period after full bloom, although sprays later in the year do not harm; they are less effective.

Preferably, GA7 is applied in the period within 10 weeks after full bloom.

Formulations

The GA7 can be formulated in a variety of ways, like powder formulation, tablet or liquid.

A suitable powder formulation is one which, when mixed with water, dissolves readily in water and forms a solution. Once the solution is formed, no further mixing or agitation of the tank-mix is required. Such wettable powder formulation is a dry, finely ground formulation. In this formulation, the active ingredient is combined with a finely ground dry carrier, usually a mineral clay, along with other ingredients that enhance the ability of the powder to be suspended in water. Upon mixing the wettable powder with water, a suspension is formed, which is then applied by a spray technique.

Tablet formulations may be effervescent, which dissolve in water over a period of two to ten minutes depending upon the type and size of the tablet. Tablets generally deliver only between 0.2-2 gram of active ingredient per tablet.

Water-soluble or water-dispersible granules are also suitable. In this type of formulation the active ingredient is formulated as granular particles of 100 to 300 micron size. To prepare the water-soluble or dispersible granules for spray application, they are completely soluble or dispersible in water upon agitation. Many different water-soluble or water-dispersible granular formulations are known for agricultural chemicals. For example, EP 0 252 897 and U.S. Pat. No. 4,936,901 disclose encapsulated plant growth regulators in water dispersible granular formulations, U.S. Pat. No. 6,387,388 B1 and U.S. Patent Application Publication US 2002/0114821 A1 disclose an extruded water-soluble insecticide, and U.S. Pat. No. 5,622,658 discloses an extrudable composition for preparing water-dispersible granules.

Other ingredients such as adjuvants may be added to the formulation. The adjuvants can facilitate spreading and efficacy, and improve the adhesion properties of the composition, and generally include oils, antifoaming agents and surfactants. Such components which are useful in the present invention include, but are not limited to: terpene, polyoxyethylene fatty alcohol ether; polyoxyethylene sorbitan esters; Silwet products (organo-silicone); octylphenol ethoxylate; ethoxylated linear alcohol polyoxyethylene fatty acid esters; sorbitan ester; modified phthalic/glycerol alkyl resin.

When the final solution is to be applied to plants which, because of their hairy or waxy surface, may be difficult to wet, it may be particularly advantageous to include such other additives, commonly known in the agrochemical industry, such as surfactants, wetting agents, spreaders and stickers. Examples of wetting agents include silicone surfactants, nonionic surfactants such as alkyl ethoxylates, anionic surfactants such as phosphate ester salts and amphoteric or cationic surfactants such as fatty acid amido alkyl betaines.

The compounds or compositions of the invention may be the sole active ingredient of the composition or they may be admixed with one or more additional active ingredients such as nematicides, insecticides, synergists, fungicides, fertilisers or plant growth regulators where appropriate. Suitable growth regulators include prohexadione calcium, chlormequat, ethephon, triazoles with growth regulation activity like metconazole and tebuconazole and the like.

The compounds or compositions of the present invention can also be used in combination with other chemical thinning agents, such as benzyladenine, 1-naphthylacetic acid, carbaryl, (2-chlorophenoxy) propionic acid, ethephon, napthaleneacetamide, thidiazuron, ammonium thiosulphate, DNOC, endothallic acid, ethephon, gibberellic acid (GA3), lime sulphur, sulfcarbamide, pelargonic acid, 6-benzylaminopurine, N-(2-chloro-4-pyridyl)-N-phenylurea, and thidiazuron.

If the GA7 compound of the invention is administered in combination optionally with one or more active agents, the GA7 may be administered consecutively, simultaneously or sequentially with each other or the one or more active agents. The major advantages of combining the compounds are that it may promote additive or possible synergistic effects through e.g. biochemical interactions. Beneficial combinations may be suggested by studying the activity of the test compounds. This procedure can also be used to determine the order of administration of the agents, i.e. before, simultaneously or after delivery.

Preferably, GA7 is applied as a liquid formulation with 0.5 to 4 wt %, like for example 1 wt % GA7. Such a liquid formulation is preferably used in an amount of 0.1 L-3 L per 100 L spraying liquid, more preferably 0.3-2 L/100 L.

The liquid formulation can be prepared by the supplier, or can be made just before use. For example, 100 gram of well dispersible powdery formulation can be dissolved in 10 L of water, which liquid can be easily mixed with the water in a spraying tank.

GA7 can be formulated by dissolution in a glycol solvent for example propylene glycol at a level of between 0.1 and 10 wt %, preferably 0.5-5 wt %, and most preferably between 1-2%. The solvent can comprise a mixture of solvents and could include an acid such as citric or adipic acid, antioxidant, inorganic salts (such as ammonium sulphate), surfactants, and/or adjuvants.

It is also possible to formulate the GA7 as a soluble powder or granule.

GA7 can be obtained by for example fermentation production using a fungal strain for example *Fusarium moniliformis*, and/or by separation of GA7 from GA4+7 by preferential crystallization using solvents.

Preferably, the water volume per hectare will be between 300-2000 L/ha and the amount of GA7 per hectare is between about 0.5-10 Liter of said liquid formulation, Preferably, the amount of GA7 applied per hectare is between 0.2-100 g/ha, preferably 10-100 g/ha.

The tests show that with suitable application of GA7, at least a 30% reduction (between 10-70%) in fruit set is achievable, and a reduction in manual thinning of at least about 30% as well.

EXAMPLES

The work has been done using with either GA7, or with a 75:25 ratio of GA7:GA4 (10 g/L overall active GA7 ingredient in a liquid formulation).

Example 1

An initial test was carried out as an evaluation trial in Piemonte with GA7 applied at 750 ml/hl on 10 mm fruitlets of peach. A better budding was obtained (especially on young lateral branches) and a high control of flowering in the following year.

Examples 2-3 and Comparative Experiment A

Trials were carried out in Italy and Spain with GA7. The trees were treated with GA7 about 3 months after full bloom in order to reduce flowering the year thereafter.

Ex 2: 2010-11 Trials Results

In Spain, trials were carried out on peach and nectarine with GA7 (>95% pure relative to GA4). The first assessments were done at harvest in 2010. These assessments did not show any impact of the treatments on yield and fruit quality. The main assessments took place in spring 2011 (i.e. the next year): The reduction of the number of buds per cm was in the order of 35% in the trials carried out in the Catalonia region. In the trials in Masso also, clear reductions of 41-78% were found depending on the variety and the dose. In the meantime, fruit size was increased. Time necessary for hand thinning was recorded in the trials done in Catalonia. The treatment with GA7 allowed a reduction of about 30% of the hand thinning time.

In Italy, a comparable trial was done. On peach and nectarine, reduction in the number of fruit/meter of branch ranged between 1.5% on Laura up to 32.9% on Sinphony with GA7 (95% pure relative to GA4) applied at 1 L/100 L ca.3 months after full bloom.

The position of the remaining buds and flowers was discussed and was not found to be a problem.

Ex 3: 2011-12 Trials Results

In 2011, new trials were started: 4 trials in peach and nectarines.

Results from one trial in nectarine showed that return bloom is reduced by the treatments on both distal and proximal part of the branches with a rate effect between 0.5 and 1 L/100 L.

| No of flowers | Untreated | 0.5 L/hL | 1 L/hL |
|---|---|---|---|
| Distal part | 11.3 | 4.7 (−58%) | 3.7 (−67%) |
| Basal part | 13.4 | 8.5 (−37%) | 5.4 (−60%) |

The other three trials clearly showed a reduction in the number of flowers per branch in the treated plots in comparison to the untreated (−17 to −50% depending on the trial and the rate).

Comparative Ex A: 2012-13 Trial

One trial was carried out in nectarine in Italy, on the same trees as the 2011 trial. GA7 1 L/hL (10 g/100 L) has been replaced by Falgro tablet at 5 tab/100 L (5 g/100 L). Thinning results were achieved, but less thinning than with GA7.

Examples 4 and 5, and Comparative Experiment B

Two trials were carried out in Spain: a timing trial and a dose rate trial. The dose rate trial was done at UFO-4 nectarines. The use of GA7 (>95% pure with respect to the presence of GA4) was applied in amounts between 0.25 and 2 L/hL at 2 months of full bloom on UFO-4 peach.

The results are as follows:

| Treatment | Number of fruit/m of long fruiting shoots (>20 cm) | Number of fruit/m of short fruiting shoots (<20 cm) | Number of fruit/m of total fruiting shoots | Total number of fruit per tree |
|---|---|---|---|---|
| Control | 23 | 33 | 24 | 735 |
| GA7 0.25 L/hL | 20 | 27 | 21 | 704 |
| GA7 0.5 L/hL | 23 | 28 | 24 | 729 |
| GA7 1.0 L/hL | 17 | 12 | 16 | 491 |
| GA7 2.0 L/hL | 13 | 7 | 12 | 375 |
| GA3 (10 g/hL)* | 18 | 29 | 19 | 675 |

*comparative experiment B

These experiments show that at comparable amounts of GA7 and GA3 (Falgro tablets), GA7 was more effective.

Further trial was executed on Merryl O Henry peach. The application of GA7 was varied over time, and in one programme GA7 was applied in two doses, 2 weeks apart.

| Treatment | Time of spray after full bloom | Number of fruit/m of long fruiting shoots (>20 cm) | Number of fruit/m of short fruiting shoots (<20 cm) | Number of fruit/m of total fruiting shoots | Total number of fruit per tree |
|---|---|---|---|---|---|
| Control |  | 8.8 | 14.5 | 13.2 | 262 |
| GA7 1 L/hL | 1.5 month | 8.6 | 5.9 | 6.5 | 149 |
| GA7 1 L/hL | 2 month | 5.1 | 3.6 | 3.8 | 77 |
| GA7 1 L/hL | 2.5 month | 3.7 | 2.8 | 3.0 | 69 |
| GA7 0.5 L/hL | 1.5 and 2 month | 4.7 | 5.8 | 5.6 | 115 |

From these experiments it is clear that GA7 is effective for thinning stone fruit, also when applied at varying times.

Examples 6-8

Ex 6: 2011 Peach Return Bloom

Shoots were divided in half and blossoms were counted according to proximal, the half closest to the tree trunk, and distal, the half closest to the shoot tip. Differences were observed for blossom counts (proximal) for both evaluation dates. GA7/4; in 75%/25% ratio at both rates showed consistently lower blossom counts throughout the trial, and a rate response was noted.

As comparison GA3 also showed consistently lower blossom counts in comparison to the UTC, and a rate response was observed for the first evaluation date, but not the second. Over the course of the trial, GA7/4 in 75/25% ratio at 100 ppm was shown to have the greatest effect at reducing total return bloom.

Ex 7: 2012 Peach Return Bloom

Once again, shoots were divided in half and blossoms were counted according to proximal and distal halves. Unlike in the 2011 evaluations, no significant treatment effects were observed in regards to number of blooms on the proximal or distal half of the fruit branches. However, when bloom counts were totaled across the entire fruiting branch (proximal+distal), a significant reduction in 2012 return bloom was observed from the FAL 900 (GA7) treatment applied at 50 ppm.

Ex 8: 2011 Peach Trial

This study consisted of 3 treatments applied on April 25, May 10, and May 26, 2011 (which is 45, 60 and 75 days after full bloom):

1. Untreated check
2. FAL 900 at a rate of 25 ppm ai (C) which is 2.5 g per 100 L, which is 0.25 L formulation per 100 L.
3. FAL 900 at a rate of 50 ppm ai (C)
4. FAL 900 at a rate of 10 ppm ai (3 treatments with 2 weeks interval)

2011-12 Observations: Evaluations consisted of assessing for firmness, soluble solids, and titratable acidity, and weight of 20 fruit per plot on end of July early August. Shoot measurements were recorded on end of February in 2011 from ten shoots per plot. The number of flowers per branch were counted from two halves (proximal and distal) of ten branches per plot on end of February 2012.

The number of flowers on the lower or proximal half of the branch (A) was significantly lowest from GA7 at 50 ppm ai (C). Flower number on the upper or distal half of the branch (B) and the average of both distal and proximal halves or ends of branches were similar among all treatments. All treatments had less flowers overall compared to the untreated control. The largest peaches were collected from GA7 at 50 ppm ai from the tree that was also producing the largest peaches in 2011. The quality of the peaches were not influenced by the treatment with GA7.

The invention has been described by reference to certain embodiments discussed above. It will be recognized that these embodiments are susceptible to various modifications and alternative forms well known to those of skill in the art without departing from the scope of the invention. Accordingly, although specific embodiments have been described, these are examples only and are not limiting upon the scope of the invention, which is defined in the accompanying claims.

The invention claimed is:

1. A method for thinning a stone fruit bearing tree, said method comprising applying a composition comprising 70% or more of GA7 and 30% or less of GA4 to the stone fruit bearing tree in the first year by foliar spray in a period of 4 to 10 weeks after full bloom, whereby thinning the stone fruit bearing tree, and wherein the stone fruit is selected from the group consisting of peach, nectarine, cherry, mirabelle, and plum.

2. The method according to claim 1, wherein the stone fruit is peach or nectarine.

3. The method according to claim 1, wherein GA7 is applied in the period of 6 to 10 weeks after full bloom.

4. The method according to claim 1, wherein GA7 is used in a formulation comprising 0.5-4 wt % GA7 calculated as pure compound.

5. The method according to claim 4, wherein GA7 is applied in a liquid formulation in an amount of formulation of 0.1 L-3 L per 100 L spraying fluid.

6. The method according to claim 5, wherein GA7 is applied in a liquid formulation in an amount of formulation of 0.3 L-2 L per 100 L spraying fluid.

7. The method according to claim 1, wherein GA7 is applied in a liquid formulation in an amount per hectare of between 0.5-10 Liter.

8. The method according to claim 1, wherein GA7 is applied in an amount calculated as GA7 of between 10-100 g/ha.

9. The method according to claim 1, wherein the composition contains less than 10% of GA4.

10. A method of growing stone fruit, said method comprising thinning a stone fruit bearing tree according to the method of claim 1, and harvesting the fruit in the second year.

11. The method of growing stone fruit according to claim 10, wherein GA7 is applied in an amount calculated as GA7 of between 10-100 g/ha.

12. A method for thinning a stone fruit bearing tree, said method comprising applying a composition comprising an admixture of GA7 and GA4 comprising 70% or more of GA7 and 30% or less of GA4 to the stone bearing tree in a first year by foliar spray in a period of 4 to 10 weeks after full bloom, whereby thinning the stone fruit bearing tree, and wherein the stone fruit is selected from the group consisting of peach, nectarine, cherry, mirabelle, and plum.

13. A method for thinning a stone fruit bearing tree, said method comprising applying a composition comprising 70% or more of GA7 and 30% or less of GA4 to the stone fruit bearing tree in the first year by foliar spray in a period of 4 to 10 weeks after full bloom, whereby thinning the stone fruit bearing tree, and wherein the stone fruit is selected from the group consisting of peach, nectarine, cherry, mirabelle, and plum, and wherein GA7 is applied at a concentration of about 10 g/hL or more in the foliar spray composition.

* * * * *